United States Patent [19]

Lecoq et al.

[11] Patent Number: 4,740,603

[45] Date of Patent: Apr. 26, 1988

[54] PROCESS FOR THE PREPARATION OF ε-CAPROLACTONE

[75] Inventors: Jean-Claude Lecoq, Chaponost; Michéle Pralus, Saint-Cyr Au Mont D'Or; Jean-Pierre Schirmann, Oullins, all of France

[73] Assignee: PCUK Produits Chimiques Ugine Kuhlmann, Courbevoie, France

[21] Appl. No.: 873,282

[22] Filed: Jun. 4, 1986

Related U.S. Application Data

[63] Continuation of Ser. No. 345,240, Feb. 3, 1982, abandoned, which is a continuation-in-part of Ser. No. 181,830, Aug. 27, 1980, abandoned.

[30] Foreign Application Priority Data

Feb. 20, 1981 [FR] France ................................ 81 03374

[51] Int. Cl.$^4$ ........................................... C07D 313/04
[52] U.S. Cl. ...................................................... 549/272
[58] Field of Search ......................................... 549/272

[56] References Cited

U.S. PATENT DOCUMENTS

| | | | |
|---|---|---|---|
| 2,877,266 | 3/1959 | Korach | 260/502 R |
| 3,064,008 | 11/1962 | Phillips et al. | 549/266 |
| 3,264,346 | 8/1966 | Weiberg et al. | 260/502 R |
| 3,517,033 | 6/1970 | Weiberg | 549/272 |
| 3,766,212 | 10/1973 | Waldmann | 549/272 |
| 4,267,124 | 5/1981 | Hardy et al. | 260/502 R |

FOREIGN PATENT DOCUMENTS

| | | |
|---|---|---|
| 691391 | 5/1967 | Belgium . |
| 0004407 | 3/1979 | European Pat. Off. . |
| 0020952 | 1/1981 | European Pat. Off. . |
| 1490173 | 6/1967 | France . |
| 1492059 | 7/1967 | France . |
| 1531053 | 6/1968 | France . |
| 2101985 | 3/1972 | France . |

*Primary Examiner*—Jane T. Fan
*Attorney, Agent, or Firm*—Pennie & Edmonds

[57] ABSTRACT

This invention relates to a process for the preparation of stable solutions of ε-caprolactone by means of the oxidation of cyclohexanone by a percarboxylic acid containing 2 to 4 carbon atoms. According to the invention, the percarboxylic acid is in the form of a crude solution, such as that resulting from the reaction of hydrogen peroxide with the corresponding carboxylic acid in the presence of a boric acid catalyst with the continuous elimination of water by azeotropic entrainment.

10 Claims, No Drawings

PROCESS FOR THE PREPARATION OF ε-CAPROLACTONE

This is a continuation of application Ser. No. 345,240, filed Feb. 3, 1982 and now abandoned, which is a continuation-in-part of application Ser. No. 181,830, filed Aug. 27, 1980 and now abandoned.

TECHNICAL FIELD

This invention relates to a process for the preparation of ε-caprolactone by means of the oxidation of cyclohexanone with a crude solution of percarboxylic acid.

BACKGROUND ART

Since its discovery in 1899, it has been well known that via the Baeyer-Villiger reaction, ketones may be oxidized to esters by means of a percarboxylic acid:

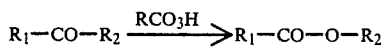

The mechanism of the reaction is such that a complex peroxidized intermediary is formed and subsequently rearranges itself according to an ionic process to yield an ester.

A particularly important application of the Baeyer-Villiger reaction is in the preparation of lactones from cyclic ketones:

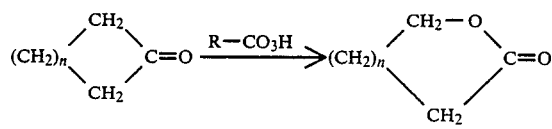

In the above reaction, when n=3, the cyclic ketone is cyclohexanone and its oxidation by percarboxylic acid yields ε-caprolactone.

It is well known that ε-caprolactone is unstable in an acidic medium. Therefore, in order to obtain this particular lactone in high yields directly from cyclohexanone via the Baeyer-Villiger reaction, it is essential that the solution of percarboxylic acid used demonstrates the weakest possible acidity. Due to this requisite factor of low acidity, the choice of method for the preparation of percarboxylic acid becomes important.

One proposed method involves the use of peroxyacetic acid which is prepared by the oxidation of acetaldehyde by oxygen. The major inconvenience of this process is the necessity of valorizing the acetic acid co-product formed during the oxidation of cyclohexanone.

Another proposed method reacts a carboxylic acid with hydrogen peroxide to prepare percarboxylic acid. Advantageously, this type of process permits the recycling of carboxylic acid after the oxidation of cyclohexanone. However, percarboxylic acid solutions obtained by the reaction of hydrogen peroxide with a carboxylic acid according to known methods all demonstrate strong acidity. This is due to the fact that the carboxylic acid used is a strong acid, such as formic acid, or that the formation of percarboxylic acid is catalyzed by a strong acid catalyst, such as sulfuric acid.

Thus, the oxidation of cyclohexanone by solutions of percarboxylic acid obtained according to these known methods necessitates neutralization of the strong acid catalyst in order to avoid adverse effects in the production of ε-caprolactone and the formation of numerous by-products. The inclusion of a neutralization step, however, leads to the precipitation of mineral salts, which are difficult to separate from the medium and which are frequently, themselves, catalysts for the degradation of ε-caprolactone.

To avoid these inconveniences, Belgium Pat. No. 540,412 and British Pat. No. 776,758 have proposed the use of an ion-exchanging resin, having strong acid groups, as a catalyst for the formation of percarboxylic acid. This catalyst is very effective and is easy to separate, but it presents a danger in that heavy metallic ions, such as $Fe^{+3}$ ions, which are known to be catalysts for the violent decomposition of percarboxylic acids and are always present in a small concentration in the organic products, become fixed to and accumulated on the resins.

Other proposed methods use pure percarboxylic acid obtained by distillation. However, these processes also present evident dangers.

SUMMARY OF THE INVENTION

The applicants have discovered that high yields of stable solutions of ε-caprolactone can be obtained via the oxidation of cyclohexanone by means of crude solutions of percarboxylic acid obtained according to the process described in U.S. patent application Ser. No. 181,830, filed on Aug. 27, 1980. The process involves reacting hydrogen peroxide with a carboxylic acid, in the presence of a boric acid catalyst such as, for example, orthoboric or metaboric acid and continually eliminating the water of the reaction by azeotropic entrainment. The inconveniences associated with the neutralization of strong acid catalysts, necessitated in the known methods for the production of caprolactones, are eliminated when the process of this invention is employed for the production of ε-caprolactone.

DETAILED DESCRIPTION OF THE INVENTION

Preparation of Crude Solutions of Percarboxylic Acid

According to the process detailed in U.S. patent application Ser. No. 181,830, filed on Aug. 27, 1980, a crude solution of percarboxylic acid is obtained by reacting a carboxylic acid with hydrogen peroxide in the presence of catalytic quantities of a boric acid such as orthoboric or metaboric acid and an azeotropic entraining solvent to permit the continuous elimination from the reaction medium of the water supplied by the aqueous solution of hydrogen peroxide as well as the water of the reaction.

Orthoboric ($H_3BO_3$) and metaboric $(HOBO)_n$ acids are well known to be weak mineral acids whose action as acids cannot be compared with that of strong acids such as sulfuric acid ($H_2SO_4$). Therefore, this process is, undoubtedly, a different catalytic process, whose nature, however, is not yet known.

The carboxylic acids with which the process is concerned are water-soluble aliphatic carboxylic acids, such as formic, acetic, propionic and butyric acids.

The azeotropic entraining agent may be advantageously selected from solvents having a boiling point of less than 100° C. which form a heteroazeotrope with water. Solvents containing chlorine, such as chloroform, carbon tetrachloride, methylene chloride, 1,2-dichloroethane, dichloropropane; solvents containing hydrocarbons, such as cyclohexane, benzene, toluene; esters, such as formates, acetates, propionates, butyrates, isobutyrates, of methyl, ethyl, propyl, isopropyl, n-butyl, represent some non-limiting examples.

The hydrogen peroxide which can be employed according to the invention can be in anhydrous form or in the form of a commercial aqueous solution having a titer of 30 to 70% by weight. It may be advantageous to add to the reaction mixture products that stabilize hydrogen peroxide, such as phosphates, polyphosphates, derivatives of ethylenediaminetetraacetic acid, etc.

The process of preparing the crude solution of percarboxylic acid, therefore, comprises reacting a carboxylic acid with hydrogen peroxide in the presence of the azeotropic entraining agent and the catalyst while continuously eliminating water from the reaction medium, by azeotropic distillation.

The temperature at which the reaction is conducted ranges between about 40° C. and 100° C.; preferably between 40° C. and 70° C. Depending on the temperature selected and the reaction system employed, the elimination can be done by operating at atmospheric pressure or under reduced pressure. The pressure may therefore range between about 20 mm of mercury and 760 mm of mercury.

The duration of the reaction depends on the nature of the catalyst, the nature of the carboxylic acid, the nature of the azeotropic entraining agent, and the reaction temperature. It may range from a few minutes to several hours. The reagents may be introduced in equimolecular quantities, but a molar excess or deficiency of one or the other of the reagents can also be utilized. For example, from about 0.1 to 10 moles of carboxylic acid per mole of hydrogen peroxide can be used, but preferably from 1 to 5 moles are used.

The catalyst is utilized in a quantity of about 0.001 to 0.1 mole of boric acid per mole of hydrogen peroxide. However, the preferred molar ratio ranges between 0.001 and 0.01 mole per mole of hydrogen peroxide introduced.

The quantity of azeotropic entraining solvent ranges between about 50 and 75% by weight of the reaction mixture, so that the boiling point of the mixture can be adjusted at will and the water eliminated efficiently.

Preparation of ϵ-Caprolactone

According to the process of this invention, stable solutions of ϵ-caprolactone are produced by the oxidation of cyclohexanone by means of crude solutions of a percarboxylic acid containing 2 to 4 carbon atoms prepared according to the process of U.S. patent application Ser. No. 181,830, detailed above. Preferred percarboxylic acids are peroxyacetic acid and perpropionic acid.

The crude solutions of percarboxylic acid used in the process of the invention comprise homogeneous solutions of peracid in the corresponding carboxylic acid which also contain, under one advantageous embodiment of the invention, organic solvents which are both compatible with the peracid and miscible with it. It is particularly advantageous to use, as an organic solvent, the same solvent that was used as the azeotropic entraining agent of the water from the preparation of the percarboxylic acid.

According to the specific peracid utilized, its proportion in the crude solution used to oxidize the cyclohexanone may be between about 5 to 40% by weight.

Under one embodiment of this invention, the crude solution of percarboxylic acid can also contain small quantities of hydrogen peroxide which have not reacted with the carboxylic acid; for example, up to about 0.1 mole of hydrogen peroxide per 100 g of crude solution of percarboxylic acid.

The oxidation of cyclohexanone by the crude solution of peracid is preferably carried out at atmospheric pressure but may also be effected at higher or lower pressures. The temperature of the reaction is between about 20° C. and 120° C.; preferably between about 40° C. and 80° C.

The molar ratio of cyclohexanone to percarboxylic acid can be between about 1 and 5; preferably between about 1 and 1.5.

The oxidation reaction may be carried out continuously or non-continuously. In the former case, one reactor or many reactors in sequence are fed simultaneously with cyclohexanone and with a crude solution of percarboxylic acid. Depending on the temperature of the reaction, residence time in the reactors varies between about 30 minutes and 4 hours.

EXAMPLES

The following examples illustrate various aspects of the process of this invention. In each example, the content of ϵ-caprolactone and cyclohexanone in the final solutions is determined by gaseous-phase chromatography, while the residual peroxidic oxygen is chemically proportioned. The examples are set forth for the purpose of illustration only and are not to be construed as limiting the scope of the invention in any manner.

EXAMPLES 1 TO 7:

PREPARATION OF CRUDE SOLUTIONS OF PERCARBOXYLIC ACID

Examples 1 to 5

Into a 250 cm$^3$ reactor equipped with a distilling column of 5 Oldershaw plates with an overhead reflux condenser, 50 g of propionic acid, 70 g of azeotropic entraining solvent, 0.2 g of catalyst and 0.1 g of disodium phosphate are introduced. This mixture is made to reflux, and 0.1 mole of hydrogen peroxide in the form of an aqueous solution of 70% by weight is progressively introduced. The condenser is designed in such a way that only the condensed organic phase is refluxed in the column, while the decanted aqueous phase is drawn off continuously. The reaction conditions and the results are shown in Table I.

Example 6

Into a 500 cm$^3$ reactor equipped with a distillation column of 10 Oldershaw plates with an overhead reflux condenser of the same type as the one described above, are placed 125 g of propionic acid, 175 g of 1,2-dichloroethane, 0.5 g of orthoboric acid ($H_3BO_3$) and 0.1 g of disodium phosphate. Reflux is induced under a pressure of 150 mm of mercury. The temperature of the reaction medium is 50° C. 0.3 mole of hydrogen peroxide, in the form of an aqueous solution of 70% by weight, is progressively added. After two hours of reaction, during which water is eliminated continuously by azeotropic distillation, the medium contains 0.24 mole of perpropionic acid as well as 0.027 mole of hydrogen peroxide, while the distilled aqueous phase contains 0.032 mole of hydrogen peroxide.

EXAMPLES 7 TO 11:

PREPARATION OF ϵ-CAPROLACTONE

Example 7

A solution of perpropionic acid is prepared according to U.S. patent application Ser. No. 181,830 (Examples 1 to 6), by the reaction of an aqueous solution of 70% hydrogen peroxide with propionic acid in the presence of 1% by weight of boric acid. At all times, the water of the reaction is continually removed by azeotropic entrainment with 1,2-dichloroethane.

The crude solution obtained has the following composition:

| | |
|---|---|
| 1,2-dichloroethane | 52.6% |
| Propionic acid | 33.0% |
| Perpropionic acid | 12.6% |
| Hydrogen peroxide | 0.8% |
| Boric acid | 1.0% |

Into a glass reactor having a volume of 250cm$^3$, equipped with an agitation system, and a refrigerant and equipped with a temperature control system, 175 g/h of a crude solution of perpropionic acid and 40 g/h of cyclohexanone are continuously introduced. The temperature of the reactor is maintained at 60° C. and the residence time of the reactants in the reactor is approximately 1 hour.

A solution containing 13.2% by weight of ε-caprolactone is produced. The conversion rate of peroxidic oxygen is 92% and the selectivity to ε-caprolactone is 94%. The obtained solution of ε-caprolactone is stable in storage at ambient temperature.

EXAMPLE 10

Into a glass reactor maintained at 50° C. and containing 6 g of cyclohexanone and 50 g of propionic acid, 50 g of a crude solution of perpropionic acid, obtained according to the process described in U.S. patent application Ser. No. 181,830 (Examples 1 to 6) are added over a period of 30 minutes. The crude solution contains 0.100 mole of perpropionic acid, 0.004 mole of hydrogen peroxide per 100 g of solution and 0.5% by weight of boric acid.

After a reaction time of 2 hours, 0.048 mole of ε-caprolactone is produced. The conversion rate of peroxidic oxygen is 94% and the selectivity to ε-caprolactone is 98%.

The stability of the obtained solution of ε-caprolactone in storage at ambient temperature is good.

EXAMPLE 11

The process of Example 10 is repeated but the crude solution of perpropionic acid is replaced by a solution containing 0.085 mole of peracetic acid, 0.005 mole of hydrogen peroxide per 100 g of solution and 0.6% by weight of boric acid.

After a reaction time of 2 hours, 0.040 mole of ε-caprolactone is produced. The conversion rate of peroxidic oxygen is 96% and the selectivity to ε-caprolactone is 92%.

The stability of the obtained ε-caprolactone solution in storage at ambient temperature is good.

TABLE 1

| Ex. | Carboxylic Acid | Catalyst | Solvent | T °C. | Pressure mm Hg | Duration min. | Remaining H$_2$O$_2$ in m moles | Peracids formed in m moles | Distilled H$_2$O$_2$ in m moles |
|---|---|---|---|---|---|---|---|---|---|
| 1. | Propionic | H$_3$BO$_3$ | Cyclohexane | 94° | 760 | 30 | 2 | 50 | 20 |
| 2. | Propionic | H$_3$BO$_3$ | Dichloroethane | 94° | 760 | 30 | 6 | 75 | 7 |
| 3. | Propionic | H$_3$BO$_3$ | Dichloroethane | 50° | 150 | 180 | 3 | 82 | 14 |
| 4. | Propionic | (HBO$_2$)$_n$ | Dichloroethane | 50° | 150 | 180 | 3.9 | 90 | 5 |
| 5. | Acetic | H$_3$BO$_3$ | Dichloroethane | 50° | 180 | 180 | 7 | 87 | 6 |

EXAMPLE 8
(COMPARATIVE EXAMPLE)

The process of Example 7 is repeated using a perpropionic acid solution obtained by the reaction of hydrogen peroxide with propionic acid in the presence of a sulfuric acid catalyst. This solution contains 0.195 mole of perpropionic acid and 0.020 mole of hydrogen peroxide per 100 g of the crude solution. The solution also contains 0.05% by weight of sulfuric acid.

The conversion rate of peroxidic oxygen is 95% and the selectivity to ε-caprolactone is only 10%.

Upon storing the obtained solution for 24 hours at ambient temperature, subsequent analysis of the solution shows no ε-caprolactone present.

EXAMPLE 9
(COMPARATIVE EXAMPLE)

The process of Example 8 is repeated using the same perpropionic acid solution obtained by sulfuric acid catalysis, which has been further neutralized by a concentrated solution of soda.

The conversion rate of peroxidic acid is 91% and the selectivity to ε-caprolactone is 81%.

After the obtained solution is stored for 24 hours at ambient temperature, the selectivity to ε-caprolactone has fallen to 40%.

We claim:

1. A process for the preparation of ε-caprolactone which comprises oxidizing cyclohexanone with a crude unpurified solution of percarboxylic acid wherein the percarboxylic acid contains 2 to 4 carbon atoms prepared by reacting hydrogen peroxide with the corresponding carboxylic acid in the presence of a boric acid catalyst and continuously eliminating water therefrom by azeotropic entrainment, said solution containing unreacted carboxylic acid, unreacted hydrogen peroxide and boric acid.

2. The process according to claim 1 wherein the percarboxylic acid comprises between about 5 to 40% by weight of the crude solution.

3. The process according to claim 2 wherein the molar ratio of cyclohexanone to percarboxylic acid is between about 1 and 5.

4. The process according to claim 3 wherein the crude solution of percarboxylic acid is a solution of peracetic acid.

5. The process according to claim 3 wherein the crude solution of percarboxylic acid is a solution of perpropionic acid.

6. The process according to claim 4 wherein the crude solution of percarboxylic acid contains an organic solvent that is miscible in and compatible with the percarboxylic acid.

7. The process according to claim 6 wherein the crude solution of percarboxylic acid contains up to about 0.1 mole of hydrogen peroxide per 100 g of solution.

8. The process according to claim 5 wherein the crude solution of percarboxylic acid contains an organic solvent that is miscible in and compatible with the percarboxylic acid.

9. The process according to claim 8 wherein the crude solution of percarboxylic acid contains up to about 0.1 mole of hydrogen peroxide per 100 g of solution.

10. A process for the preparation of epsilon caprolactone which comprises oxidizing cyclohexanone with a crude unpurified solution of percarboxylic acid comprising between about 5-40% by weight of the crude solution wherein the percarboxylic acid contains 2 to 4 carbon atoms and further wherein the molar ratio of cyclohexanone to percarboxylic acid is between about 1 and 5 and wherein the percarboxylic acid is prepared by reacting hydrogen peroxide with the corresponding carboxylic acid in the presence of a boric acid catalyst and continuously eliminating water therefrom by azeotropic entrainment, said solution containing unreacted carboxylic acid, unreacted hydrogen peroxide and boric acid.

* * * * *

UNITED STATES PATENT AND TRADEMARK OFFICE
CERTIFICATE OF CORRECTION

PATENT NO. : 4,740,603
DATED : Apr. 26, 1988
INVENTOR(S) : Jean-Claude Lecoq, Michele Pralus and Jean-Pierre Schirmann It is certified that error appears in the above-identified patent and that said Letters Patent is hereby corrected as shown below:

In column 1, line 8, after "now", delete "abandoned" and insert --issued on Jul. 6, 1982 as U.S. Pat. No. 4,338,269 --.

Signed and Sealed this

Eleventh Day of October, 1988

Attest:

DONALD J. QUIGG

Attesting Officer

Commissioner of Patents and Trademarks